United States Patent [19]
Bittle et al.

[11] 3,944,469
[45] Mar. 16, 1976

[54] FELINE CALICIVIRUS VACCINE AND PRODUCTION THEREOF

[75] Inventors: James Long Bittle, Doylestown, Pa.; Wayne J. Rubic, Titusville, N.J.

[73] Assignee: Pitman-Moore, Inc., Washington's Crossing, N.J.

[22] Filed: Nov. 21, 1974

[21] Appl. No.: 525,689

[52] U.S. Cl. .................................. 195/1.3; 424/89
[51] Int. Cl.$^2$ ........................................ A61K 39/12
[58] Field of Search ....................... 424/89; 195/1.3

[56] References Cited
OTHER PUBLICATIONS

Burki, Arch. F. die Gesam, Vir. 15: 690–696 (1965) "Picornoviruses of Cats."
Burki, J.A.V.M.A. 158 (6, pt. 2): 916–919, Mar. 15, 1971, "Virologic and Immunologic Aspects of Feline Picornaviruses."
Lee et al., Infect. Immun. 7(4): 678–679, Apr. 1973, "Thermal and pH Hydrogen–Ion Concentration Stability of Feline Calicivirus."
Hoover et al., Vet. Pathol. 10(4): 307–322 (1973), "Lesions Produced by Feline Picornaviruses of Different Virulence in Pathogen–Free Cats."
Gillespie et al., Advances in Vet. Sci. & Comp. Med. (1973). Vol. 17, pp. 176–188, "Feline Calicivirus Infection."
Povey et al., J. Comp. Path. 84: 245–256 (1974) "Experimental Infections with Feline Caliciviruses (Picornaviruses) in Specific–Pathogen–Free Kittens."
Povey, Infect. Immun. 10(6): 1307–1314, Dec. 1974, "Serological Relationships Among Feline Caliciviruses."
Hoover et al., J.A.V.M.A. 166(5): 463–468, Mar. 1, 1975, "Experimentally Induced Feline Calicivirus Infection Clinical Signs and Lesions."

*Primary Examiner*—Shep K. Rose
*Attorney, Agent, or Firm*—Salvatore R. Conte

[57] ABSTRACT

The propagation and modification of feline calicivirus (FCV) in feline tissue cultures and the development of a vaccine useful for the prevention of feline calicivirus respiratory infections in cats, said vaccine comprising a modified virus strain of FCV.

9 Claims, No Drawings

FELINE CALICIVIRUS VACCINE AND PRODUCTION THEREOF

BACKGROUND OF THE INVENTION

Feline calicivirus infection is a common and serious disease of cats usually associated with the respiratory tract. There has been many serotypes reported in the literature as causing from slight respiratory problems to severe pneumonia in cats. Reports in the literature indicate that this disease is responsible for approximately half the clinical cases of feline respiratory infections. The virus infects the epithelial cells of the nose, lung, pharynx, trachea and eye, causing epitheliolysis and necrosis. Resultant signs vary from inapparent infection to mild respiratory disease to severe respiratory disease with pneumonia and sometimes death. Further ulcerative lesions of the nose and tongue are often associated with the disease as are anorexia and pyrexia. The virus is shed from the nose, eyes and mouth through the course of the clinical disease. Feline calicivirus infections are often severe and complicated further by bacteria when resistance becomes low. Mortality may be significant, especially in young kittens. The transmission of feline calicivirus to susceptible cats is generally by intranasal instillation, for example, by droplets expelled in sneezing or by contact (usually nose to nose). Resistance following recovery from natural or experimental infection is of moderate duration.

The FCV group of serotypes was formerly called Picorna virus. This name was changed by the International Committee on viral nomenclature in 1971 designating this viral group as Picorna viradae in the genus calicivirus. The first isolation of a feline calicivirus serotype was reported by L. B. Fastier in Amer. J. Vet. Res., 18, 382 (1957). Since then, several reports have appeared in the literature which confirm the isolation of feline calicivirus from feline subjects in various parts of the world which identify the virus as a feline member of calicivirus, and which describe the transmission, epidemiology and histologic characteristics of the disease, as well as the infections observed from different serotypes. For example, see J. L. Bittle et al., Amer. J. Vet. Res., 21, 547 (1960) and 22, 374 (1961); F. Burki, Arch. F. die Gesam. Vir., 15, 690 (1965); R. A. Crandall, Proc. Soc. Exptl. Biol. & Med. 126, 240 (1967); Kahn & Gillespie, Cornell Vet., 60, 669 (1970); Holzinger & Kahn, Amer. J. Vet. Res., 31, 1623 (1970); and E. Takahashi et al., Jap. J. Vet. Sci., 33, 81 (1971).

An excellent up-to-date review is provided by Gillespie and Scott in the book, "Advances in Veterinary Science and Comparative Medicine," Volume 17, Edtd. by C. A. Brandly and C. E. Cornelius, pages 176–188, Academic Press, Inc., New York, 1973. Previous attempts at immunization with feline calicivirus are termed impractical by Gillespie & Scott (page 189). To date, no effective vaccine is available for protecting cats against feline calicivirus.

DESCRIPTION OF THE INVENTION

In accordance with the present invention, it has been found that feline calicivirus (FCV) can be propagated in feline tissue cultures, preferably kidney and tongue, and the virulence of the virus so modified and reduced that no symptoms of the disease are observed upon parenteral inoculation.

Accordingly, the present invention produces a modified or attenuated strain of live, feline calicivirus which when parenterally inoculated, preferably intramuscularly, into cats, it immunizes the cats to virulent FCV disease. A vaccine is also provided which is attenuated to an extent that it will stimulate an antibody response effectively immunizing the cats for prolonged periods.

The vaccine is safe in that it will not cause disease in cats that receive it by the parenteral route nor will the modified feline calicivirus pass from the vaccinated cat to other cats in contact with it, thereby eliminating the possibility of increasing the virulence of the virus by animal passage. This constitutes a significant advance in the control of disease due to feline calicivirus.

Live, virulent feline calicivirus can be obtained from cats infected with the virus according to methods of isolation and identification described in the literature [e.g., see J. B. Bittle et al., Amer. J. Vet. Res., 21, 547 (1960]. The preferred serotypes of feline calicivirus for utilization in this invention are those which are serologically related as determin by conventional techniques, e.g., cross serum-neutralization tests. On page 183 (Table I) of Gillespie and Scott (ibid.), a listing of several feline calicivirus serotypes is shown. Among the most preferred for purposes of this invention are the two serotypes designated as "F-9" and "F-S". the F-9 strain has been deposited in American Type Culture Collection (ATCC) No. VR-782.

In general, virus isolations can be made by swabbing the nasal and conjuntival membranes of infected cats with moist, sterile, cotton swabs which are then placed in a suitable feline tissue culture medium, followed by standard serial passages in order to replicate and isolate the virus. A particularly suitable culture medium is one derived from the cortical tissue of kidneys from 8- to 12-week old kittens which is trypsinized by a method similar to that described by J. Youngner [Proc. Soc. Exptl. Biol. & Med., 85, 202 (1954)] for monkey kidney cells.

In preparing the vaccines of this invention, it has been found that attenuation and modification of the virulent feline calicivirus can be readily accomplished by a relatively few, at least about 10, preferably at least 13, and generally about 13 to 35, serial passages, including purification by standard terminal dilution techniques, in feline tissue utilizing lower incubation temperatures of about 30° ± 2°C, preferably 29°–31°C. Purification of the viral preparations may be accomplished by conventional tube or plague methods during or following the course of serial passages.

Feline calicivirus is capable of propagation in such feline tissue culture systems, for example, lung, testicle, kidney, thymus, tongue and embryonic fetal tissue, and also in established cell lines, such as, for example, Crandall's cat kidney cell line (CrFK), cat tongue cell lines, e.g., at the third passage level (Fc3Tg), and feline neurofibrosarcoma cell line (FNFS). Feline tongue cell lines are most preferred.

The passage time intervals should be such as to sufficiently allow the virus to replicate between passages, preferably from 1 to 6 days. The optimum passage time interval can readily be determined by standard techniques, for example, by cytopathic observations, such as by allowing the virus to grow during a particular passage prior to the point where a gross cytopathic effect (CPE) can be observed while continuing incubation.

The obtention of successful vaccines by the present low passage-low temperature method is rather surprising in view of the fact that serial passage in feline tissue at normal incubation temperatures, about 35°–37°C., does not alter or modify the virus or its pathogenicity at approximately the same number of passages.

In accordance with this invention, therefore, a process is provided for attenuating virulent feline calicivirus (FCV) for the production of a vaccine capable when injected into cats of immunizing them against FCV which comprises introducing an inoculum of virulent FCV into a nutrient fluid feline tissue culture medium which is non-toxic to said virus, propagating said virus by incubating said nutrient tissue culture medium at a temperature of about 30° ± 2°C. for a period of 1 to 6 days, and thereafter separating an inoculum of said virus and serially passing the virus through other such feline tissue cultures for a total of at least about 10 passages.

The viral preparations produced by this invention may be diluted to adjust their potency, and they may have added to them stabilizers, such as dextrose and lactose, or other non-toxic substances. The viral preparations may also be desiccated, e.g., by freeze drying, for storage purposes or for subsequent formulation into liquid vaccines. Stabilizers useful in the freeze drying of viruses are described in W. A. Rightsel et al., Cryobiology, 1967, 3:423 and D. Greiff et al., *Advances in Freeze Drying*, L. Rey, Ed., pp. 103–122, Hermann, Paris, 1966. In addition, the vaccines may be utilized in a mixture with other immunogenic vaccines for administration to cats.

The manner in which our invention is carried out is described in greater detail in conjunction with the following specific experiments. It is understood that these specific experiments are by way of illustration, and not by limitation.

EXAMPLE I

A sample of live virulent feline calicivirus (F-9 serotype, ATCC No. VR-782), cultured and isolated according to the procedure described by J. L. Bittle et al., Amer. J. Vet. Res., 21, 547, (1960), is added to monolayers of a feline diploid tongue cell line in standard culture tubes or leighton tubes (16 × 125 mm) prepared as follows. The tongue cell line used is the Fc3Tg line referred to in K. M. Lee et al., Cornell Veterinarian, 59, 539 (1969). Each cell line tube, containing 1–2 ml of growth medium consisting of Eagles Minimum Essential Medium (MEM) supplemented with 10% fetal calf serum, 0.1% lactalbumin hydrolysate, 30 units penicillin, 30 mcg streptomycin and 2.5 mcg amphotericin, is seeded with 1 ml feline tongue cells (200,000 cells per ml). If necessary, the pH is adjusted with sodium bicarbonate to maintain a pH of about 7.2–7.8. The cells are allowed to grow at about 35° ± 2°C until a monolayer of cells is achieved. Fluids are then poured off and 1–2 ml of a maintenance medium (same as above except that 1–2% fetal calf serum is utilized) is added. About 4 to 6 such tubes are utilized per viral passage.

To each tissue culture tube is added the F-9 feline calicivirus inoculum. The thus-seeded tube is maintained at about 29°–31°C until a cytopathic effect (CPE) is observed by microscopic examination (about 2–7 days). When the CPE reaches about 75–90 percent of the monolayer, the contents of the tube are harvested and 0.2 ml inoculums are subjected to identical serial passages for 6 additional passages (7 passages total). After the 7th passage, a standard terminal dilution purification is performed utilizing Eagles MEM supplemented with the aforementioned antibiotics as the diluent with incubation maintained at 29°–31°C. After 7 days, the final tube which is positive with 75–90% CPE is harvested and the entire procedure repeated twice for a total of 10 passages. An 11th passage is performed for purposes of increasing volume by inoculating a 0.5 ml sample from the 10th passage into flasks containing monolayers of feline diploid tongue cell cultures obtained by propagation of the tongue cells as previously described. At the end of the 11th passage, the pool is harvested, identified and titrated by known methods.

The pool thus prepared constitutes a bulk vaccine which may be diluted according to the titer or may have added thereto stabilizers or other nontoxic substances. For use as a vaccine, it may be desiccated or it may be prepared in liquid form.

In propagating and attenuating the virus, any nontoxic nutrient fluid tissue culture medium may be utilized. In addition to the supplemented Eagles MEM medium described above, it will be understood that other nontoxic nutrient fluid tissue culture mediums may also be used.

EXAMPLE II

1 Ml of a vaccine prepared according to Example I and titrated to a virus titer at 35° ± 2°C of $10^{4.1}$ $TCID_{50}$/ml (determined by CPE) is administered intramuscularly to three susceptible cats. Two other cats are maintained as unvaccinated controls. All 5 cats are previously determined to be sero-negative to feline calicivirus. Evidence of severe FCV disease is generally observed starting with pyrexia on the second day and other clinical signs seen from about the fourth day onward after normal contact or challenge with virulent feline calicivirus. The antibody titer of all 5 cats prior to vaccination is less than 1:3 and one month later, just prior to challenge, the antibody titer of the 3 inoculated cats averages 1:15 as compared to less than 1:3 for the 2 unvaccinated controls. All 5 cats are challenged intranasally with virulent feline calicivirus (F-9 serotype) applied by a nebulizer (each cat in an enclosed atmosphere; total dose of 0.025 ml containing about $10^6$ $TCID_{50}$). The cats are observed for three weeks for evidence of clinical disease. All of the three vaccinated cats remain normal with no clinical disease or symptoms in contrast to the two unvaccinated controls which become very ill with FCV disease exhibiting typical symptoms such as febrile response, running eyes and nose, lack of appetite and general malaise.

EXAMPLE III

Live virulent feline calicivirus, cultured and isolated according to the procedure described by J. L. Bittle et al., ibid., and denoted by said investigators as an F-9 isolate, was serially passed 7 consecutive times in primary feline kidney tissue cultures at 1–6 day intervals at about 35°C., followed by 3 successive terminal dilutions in similar tissue cultures for a total of 10 passages (virulent virus). The virus was then adapted to a feline tongue cell line (Fc3Tg) at 37°C. (11th passage). Three additional passages were made in CrFK cells at 37°C. The 14th passage virus was tested in cats and found to cause typical clinical signs of FCV infection (virus is still virulent).

The 11th passage virus (designated P-O) was also passed in tubes containing a feline tongue cell line (Fc3Tg cells) at 29°–31°C. for a total of 8 successive passages (P-8) at 1–6 day intervals followed by 3 successive terminal dilutions (P-11) in similar tongue cultures at this temperature. Two additional passages (P-13) were made to provide a pool followed by two more passages (P-15) which was used as a master seed. Five further passages (P-20) were performed to build up volume. The P-13, P-15 and P-20 viral passages were identified by serum neutralization tests with specific F-9 goat antiserum. Vaccination of cats with said P-13, P-15 and P-20 viral passages produce significant amounts of protective antibodies enabling the animals to resist virulent feline calicivirus.

EXAMPLE IV

1 Ml of the vaccine prepared in Example III (P-20 passage) and having a virus titer at 35°C. of about $10^{5.5}$ TCID$_{50}$/ml (determined by CPE) was administered intramuscularly to four cats which were previously determined to be sero-positive to FCV (serotype unknown). The mean titer before vaccination was determined to be about 1:64 and the mean titer one month after vaccination was found to be about 1:292. Two of the cats were challenged with virulent feline calicivirus [FPV-255 serotype; see Kahn & Gillespie, Cornell Vet., 60, 669 (1970) and Amer. J. Vet. Res., 32, 521 (1971); and Holzinger & Kahn, Amer. J. Vet. Res., 31, 1623 (1970); sample received from Kahn] at 3½ months and the other two cats at 5 months. The challenge was applied with a nebulizer as described in Example II. For three weeks post challenge the cats were observed daily with no clinical signs of disease observed. In contrast, unvaccinated controls exhibited typical severe manifestation of FCV disease. This example shows that a simple dose of vaccine given to already exposed cats increased antibody formation about 4–5 times, and, when challenged with virulent feline calicivirus, the animals were protected.

EXAMPLE V

500 Ml of the virus material obtained at the P-20 passage level described in Example III was added to 500 ml of N-Z amine lactose glutamate stabilizer and dispensed into standard vaccine vials that were dried by conventional freeze-drying procedures. For inoculation purposes, the vials were reconstituted with 1 ml pyrogen-free sterile distilled water (mean titer about $10^{5.3}$ TCID$_{50}$/ml). Prior to vaccination, all experimental cats were found to have an antibody titer of less than 1:2. 1 Ml of the thus-prepared vaccine was administered intramuscularly to ten susceptible cats with five other unvaccinated cats maintained as controls. One month later, the ten vaccinated cats were given an identical booster dose intramuscularly. Antibody determinations before and two weeks after the booster inoculation, as shown below, resulted in about a 7-fold increase in antibody formation.

|            | Before Booster | 2 Weeks After Booster |
|------------|----------------|------------------------|
| Cat No. 1  | 1:3            | 1:93                   |
| Cat No. 2  | 1:23           | 1:370                  |
| Cat No. 3  | 1:30           | 1:837                  |
| Cat No. 4  | 1:8            | 1:40                   |
| Cat No. 5  | 1:40           | 1:70                   |
| Cat No. 6  | 1:70           | 1:120                  |
| Cat No. 7  | 1:53           | 1:70                   |
| Cat No. 8  | 1:4            | 1:14                   |
| Cat No. 9  | 1:53           | 1:471                  |
| Cat No. 10 | 1:53           | 1:160                  |
|            | 1:34 (mean)    | 1:225 (mean)           |

In addition to the preparation of the instant vaccines from live virulent feline calicivirus, this invention is also concerned with the preparation of a FCV vaccine using the virus, preferably the F-9 serotype, that has been modified by the method heretofore described. It would be commercially impractical for the preparation of a vaccine to use as the starting material for each new batch of vaccine live virulent feline calicivirus obtained from infected cats and then go through the requisite serial passages in order to acquire the modified virus for use as a vaccine. This invention, therefore, embodies the method of preparing a FCV vaccine which comprises using as the starting virus one that has already been modified by serial passages in feline tissue cultures as previously described, that is, a "seed" virus from a master batch of attenuated virus. Accordingly, there is herein provided a process of preparing a feline calicivirus vaccine which comprises propagating an attenuated feline calicivirus, which attenuated virus is produced by the process heretofore described, by sufficient serial passages at an incubation temperature of about 32°–37°C. in a suitable nutrient fluid feline tissue culture medium which is non-toxic to said virus until said fluid medium contains from about $10^3$ to about $10^8$ tissue culture infectious doses of said attenuated virus per ml and harvesting the fluid vaccine.

By use of the procedures described herein, a modified feline calicivirus can be readily cultivated in large quantities and in high concentrations. Using feline tissue culture propagated modified feline calicivirus, for example, the F-9 serotype, in concentrations of at least about $10^3$, and generally from about $10^3$ to about $10^8$, tissue culture infectious doses of virus per 1.0 ml of final vaccine, and by parenterally administering 1 ml of such vaccine to cats, there is stimulated in such vaccinated cats the production of protective FCV antibodies comparable to those produced by natural infections without producing the usual pathological symptoms of disease due to feline calicivirus. The vaccinated cats are also able to resist challenges with the disease-producing virus.

A marked increase in the antibody response has been observed upon the parenteral administration of a second, and even a third or more, "booster" dose of the instant vaccines. For example, it has been found that beneficial results are obtained when a second intramuscular injection is given about two weeks following the initial vaccination. For best results, it is recommended that the second injection be given not sooner than about 3–4 weeks following the first injection.

As a further feature of this invention, it has been found that enhancement of antibody production can be accomplished, in addition to the aforementioned parenteral administration of booster doses of the instant vaccines, by the exposure of cats, which have been previously immunized by parenteral administration, preferably I.M., of the instant vaccines, to feline calicivirus, for example, the F-9 serotype, by the intranasal route, which virus either has been modified according to the present invention or it is in its non-modified virulent form.

Such intranasal instillation following parenteral vaccination produces significantly high levels of antibodies that persist for long periods of time. For example, when such treated animals are challenged with virulent virus, the protection afforded is much more solid, as demonstrated by the lack of clinical disease symptoms after challenges with high tissue culture infectious doses of virulent, nonmodified feline calicivirus. For best results, it is recommended that a sufficient time elapse for the cat to become sensitized after the initial parenteral vaccination in order to develop at least a minimal degree of immunity as reflected by increased antibody formation before subjecting the animal to the subsequent intranasal contact with virulent FCV. Preferably, the intranasal instillation is given within 2–5 weeks following the initial parenteral vaccination.

Intranasal instillation is readily accomplished by inhalation of the feline calicivirus either by conventional aerosol formulations sprayed into the nasal passages or by droplets applied to the outer nostrils or in the nasal passages. A suitable concentration of feline calicivirus, for example, the F-9 serotype, whether modified as described hereinbefore or in its live virulent unattenuated form, for intranasal instillation purposes following initial vaccination by parenteral administration is from about $10^3$ to about $10^8$ tissue culture infectious doses per ml.

It is believed that the initial vaccination by the parenteral route followed by contact with FCV, either modified or not, by the respiratory route constitutes a novel method of immunization against feline calicivirus. Such method provides the animal with a humoral antibody response and a local immunity to the respiratory tract that is much more protective against disease due to FCV. Thus, a means is provided fo effective, long-lasting protection against most serotypes of FCV.

EXAMPLE VI

1 Ml of the vaccine prepared in Example III (P-20 passage level) and having a virus titer at 35°C of about $10^{5.5}$ TCID$_{50}$/ml was administered intramuscularly to a susceptible cat (Cat A) which was previously determined to be sero-negative to FCV. One other cat was maintained as an unvaccinated control. One month after the initial inoculation date, the vaccinated cat was given a second 1 ml injection intramuscularly. About 3½ months after the initial inoculation date, the vaccinated cat and the unvaccinated control were subjected to intranasal instillation of >$10^3$ TCID$_{50}$ of virulent feline calicivirus (FPV-255) with a nebulizer as similarly performed in Example II. The following results were obtained, indicating a significantly higher antibody response and lack of clinical disease symptoms when intranasal administration of the virus follows parenteral vaccination.

| | Antibody Response | | |
|---|---|---|---|
| | Titer at time of Intranasal Instillation | Titer One Month after Intranasal Instillation | Clinical Symptoms after Intranasal Instillation |
| Cat A | 1:18 | 1:180 | none |
| Control | <1:2 | 1:120 | severe |

The foregoing Example VI demonstrates the feature of this invention whereby cats are afforded effective long-lasting immunization against FCV by the process which comprises first administering parenterally to a cat a vaccine of at least about $10^3$ tissue culture infectious doses of an attenuated feline calicivirus, preferably the F-9 serotype, which virus was attenuated by at least 10 one- to six-day serial passages through feline tissue cultures in a nutrient fluid at an incubation temperature of about 30° ± 2°C, followed by a subsequent administration to said cat by the respiratory route of from about $10^3$ to about $10^8$ tissue culture infectious doses of feline calicivirus in its live virulent unattenuated form. Similar results are also obtainable with the respiratory administration of from about $10^3$ to about $10^8$ tissue culture infectious doses of feline calicivirus which has been attenuated according to the methods of this invention.

What is claimed is:

1. A process of attenuating virulent feline calicivirus which comprises propagating said virus for at least 10 one- to six-day serial passages through feline tissue cultures in a nutrient fluid at an incubation temperature of about 30° ± 2°C.

2. A process of attenuating virulent feline calicivirus for the production of a vaccine capable when injected into cats of immunizing them against feline calicivirus which comprises introducing an inoculum of live infectious feline calicivirus into a nutrient fluid culture medium which is non-toxic to said virus and contains viable feline tongue cells, propagating said virus by incubating said inoculated fluid medium at a temperature of about 30° ± 2°C for a period of 1 to 6 days and thereafter separating an inoculum of said virus therefrom and serially passing the virus through other such feline tongue cultures for a total of at least about 10 passages.

3. The process of claim 2 wherein said feline calicivirus is the F-9 serotype.

4. A process of preparing a feline calicivirus vaccine which comprises attenuating live infectious feline calicivirus by serially passing said virus through at least 10 nutrient fluid feline tissue cultures at an incubation temperature of about 30° ± 2°C until a virus titer of at least about $10^3$ tissue culture infectious doses of virus per milliliter is obtained and harvesting the fluid vaccine.

5. A process of preparing a feline calicivirus vaccine which comprises attenuating live infectious feline calicivirus serotype F-9 by serially passing said virus through at least 10 nutrient fluid cultures containing viable feline tongue cells at an incubation temperature of about 30° ± 2°C until a virus titer of from about $10^3$ to about $10^8$ tissue culture infectious doses of virus per milliliter is obtained and harvesting the fluid vaccine.

6. A process of preparing a feline calicivirus vaccine in dry solid form which comprises attenuating live infectious feline calicivirus by at least 10 one- to six-day serial passages through feline tissue cultures in a nutrient fluid at an incubation temperature of about 30° ± 2°C until a virus titer of at least about $10^3$ tissue culture infectious doses of attenuated virus per ml is obtained and drying at low temperature the thus-obtained attenuated virus-containing fluid.

7. The process of claim 6 wherein said feline calicivirus is the F-9 serotype.

8. A process of preparing a feline calicivirus vaccine which comprises propagating an attenuated feline calicivirus, which attenuated virus is obtained according to the process of claim 1, by sufficient serial passages through feline tissue cultures in a nutrient fluid at an incubation temperature of about 32°–37°C until said fluid medium contains from about $10^3$ to about $10^8$ tissue culture infectious doses of attenuated virus per ml and harvesting the fluid vaccine.

9. The process of claim 8 wherein said feline calicivirus is serotype F-9.

* * * * *